(12) United States Patent
Fujii et al.

(10) Patent No.: US 11,466,306 B2
(45) Date of Patent: Oct. 11, 2022

(54) METHOD FOR ISOLATING SPECIFIC GENOMIC REGIONS WITH USE OF MOLECULE CAPABLE OF SPECIFICALLY BINDING TO ENDOGENOUS DNA SEQUENCE

(71) Applicant: OSAKA UNIVERSITY, Osaka (JP)

(72) Inventors: Hodaka Fujii, Osaka (JP); Toshitsugu Fujita, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 477 days.

(21) Appl. No.: 14/767,068

(22) PCT Filed: Sep. 6, 2013

(86) PCT No.: PCT/JP2013/074107
§ 371 (c)(1),
(2) Date: Oct. 21, 2015

(87) PCT Pub. No.: WO2014/125668
PCT Pub. Date: Aug. 21, 2014

(65) Prior Publication Data
US 2016/0138081 A1   May 19, 2016

(30) Foreign Application Priority Data

Feb. 14, 2013 (JP) .............................. JP2013-026310
Jul. 9, 2013 (JP) .............................. JP2013-143282

(51) Int. Cl.
| | | |
|---|---|---|
| C12Q 1/68 | (2018.01) | |
| C12Q 1/6806 | (2018.01) | |
| C12N 15/10 | (2006.01) | |
| G01N 33/53 | (2006.01) | |
| C12Q 1/6809 | (2018.01) | |

(52) U.S. Cl.
CPC ....... *C12Q 1/6806* (2013.01); *C12N 15/1034* (2013.01); *G01N 33/5308* (2013.01); *C12Q 1/6809* (2013.01)

(58) Field of Classification Search
CPC .............. C12Q 1/6806; C12Q 1/6809; C12N 15/1034; C12N 2310/20; G01N 33/5308
See application file for complete search history.

(56) References Cited

U.S. PATENT DOCUMENTS

| | | | | |
|---|---|---|---|---|
| 8,697,359 | B1 * | 4/2014 | Zhang ...................... | C12N 9/22 435/6.1 |
| 2011/0239315 | A1 | 9/2011 | Bonas et al. | |
| 2012/0064620 | A1 | 3/2012 | Bonas et al. | |
| 2012/0122205 | A1 | 5/2012 | Bonas et al. | |
| 2012/1110685 | | 5/2012 | Bonas et al. | |
| 2012/0164689 | A1 * | 6/2012 | Fujii .................. | C12N 15/1086 435/91.1 |
| 2013/0217119 | A1 | 8/2013 | Bonas et al. | |
| 2014/0068797 | A1 * | 3/2014 | Doudna ............... | C12N 15/102 800/18 |

FOREIGN PATENT DOCUMENTS

| | | |
|---|---|---|
| JP | 2009-19762 | 1/2009 |
| JP | 2012-514976 | 7/2012 |
| WO | 2004/106550 | 12/2004 |
| WO | 2009/024781 | 2/2009 |
| WO | 2010/093860 | 8/2010 |
| WO | 2011/021684 | 2/2011 |

OTHER PUBLICATIONS

Dejardin et al., CEII, 2009, vol. 136, pp. 175-186.*
Dejardin et al., CEII, 2009, vol. 136(1) pp. 174-186.*
Cermak et al., Nucleic Acids Research, 2011, pp. 1-11.*
Furey in "ChIP-seq and beyond: new and improved methodologies to detect and characterize protein—DNA interactions" ( Nature Dec. 2012 vol. 13, pp. 840-852). (Year: 2012).*
Carroll reference entitled A CRISPR Approach to Gene Targeting; Mol Ther Sep. 4, 2012, vol. 20, No. 9, pp. 1658-1660). (Year: 2012).*
Fujita & Fujii in "Efficient isolation of specific genomic regions retaining molecular interactions by the iChIP system using recombinant exogenous DNA-binding proteins" (BMC Molecular Biology 2014, vol. 15, No. 26, pp. 1-8). (Year: 2014).*
Mali et al "Cas9 as versatile tool for engineering biology" (Nature Methods vol. 10, No. 10, Oct. 2013: pp. 957-963). (Year: 2013).*
Fujii & Fujita (Int. J. Mol. Sci. 2015, vol. 16, pp. 21802-21812). (Year: 2015).*
Fujita et al ("bioRxiv" (preprint posted online Nov. 30, 2015). (Year: 2015).*
International Preliminary Report on Patentability dated Mar. 19, 2015 in International (PCT) Application No. PCT/JP2013/074107, English translation.
International Search Report dated Dec. 10, 2013 in International (PCT) Application No. PCT/JP2013/074107.
Hoshino et al., "Insertional chromatin immunoprecipitation: A method for isolating specific genomic regions", Journal of Bioscience and Bioengineering, vol. 108, No. 5, 2009, pp. 446-449.

(Continued)

*Primary Examiner* — Catherine S Hibbert
(74) *Attorney, Agent, or Firm* — Wenderoth, Lind & Ponack, L.L.P.

(57) ABSTRACT

A method comprising (A) fragmenting genomic DNA in a state where the interaction of the genomic DNA and molecules interacting therewith is maintained, and (B) bringing genomic DNA into contact with an exogenous molecule capable of binding to a specific endogenous DNA sequence in the genomic DNA. According to the method, with the use of an endogenous DNA sequence present inside or in the vicinity of a target genomic region in cells to be analyzed, any genomic region can be specifically isolated in a state where the interaction of the genomic region and molecules interacting therewith is maintained, without the need of inserting a recognition sequence of an exogenous DNA-binding molecule into the vicinity of the target genomic region in the cells to be analyzed.

5 Claims, 7 Drawing Sheets
Specification includes a Sequence Listing.

(56) References Cited

OTHER PUBLICATIONS

Jinek et al., "A programmable dual-RNA-guided DNA endonuclease in adaptive bacterial immunity", Science, vol. 337, Aug. 17, 2012, pp. 816-821.
Déjardin et al., "Purification of proteins associated with specific genomic loci", Cell, vol. 136, Jan. 9, 2009, pp. 175-186.
Fujita et al., "Efficient isolation of specific genomic regions and identification of associated proteins by engineered DNA-binding molecule-mediated chromatin immunoprecipitation (enChIP) using CRISPR", Biochemical and Biophysical Research Communications, vol. 439, Aug. 11, 2013, pp. 132-136.
Fujita et al., "Identification of telomere-associated molecules by engineered DNA-binding molecule-mediated chromatin immunoprecipitation (enChIP)", Scientific Reports, vol. 3:3171, 2013, pp. 1-7.
Solomon et al., "Mapping protein-DNA interactions in vivo with formaldehyde: evidence that histone H4 is retained on a highly transcribed gene", Cell, vol. 53, Jun. 17, 1988, pp. 937-947.
Solomon et al., "Formaldehyde-mediated DNA-protein crosslinking: a probe for in vivo chromatin structures", Proc. Natl. Acad. Sci. USA, vol. 82, Oct. 1985, pp. 6470-6474.
Dekker et al., "Capturing Chromosome Conformation", Science, vol. 295, 2002, pp. 1306-1311.
Simonis et al., "Nuclear organization of active and inactive chromatin domains uncovered by chromosome conformation capture-on-chip (4C)", Nature Genetics, vol. 38, No. 11, Nov. 2006, pp. 1348-1354.
Simonis et al., "An evaluation of 3C-based methods to capture DNA interactions", Nature Methods, vol. 4, No. 11, Nov. 2007, pp. 895-901.
Griesenbeck et al., "Affinity purification of specific chromatin segments from chromosomal loci in yeast", Molecular and Cellular Biology, vol. 23, No. 24, Dec. 2003, pp. 9275-9282.
Fujita et al., "Direct identification of insulator components by insertional chromatin immunoprecipitation", PLoS One, vol. 6, issue 10, Oct. 2011, e26109.
Lambert et al., "Defining the budding yeast chromatin-associated interactome", Molecular Systems Biology, vol. 6, No. 448, 2010, pp. 1-16.
Jamieson et al., "Drug discovery with engineered zinc-finger proteins", Nature Reviews, vol. 2, May 2003, pp. 361-368.
Bogdanove et al., "TAL Effectors: Customizable Proteins for DNA Targeting", Science, vol. 333, 2011, pp. 1843-1846.
Taberner et al., "Yeast karyopherin Kap95 is required for cell cycle progression at Start", BMC Cell Biology, vol. 11, No. 47, 2010, pp. 1-13.
Extended European Search Report dated Nov. 9, 2016 issued in corresponding European Patent Application No. 13875109.4.
V. Orlando, "Mapping chromosomal proteins in vivo by formaldehyde-crosslinked-chromatin immunoprecipitation" Trends in Biochemical Sciences, Mar. 1, 2000, vol. 25, No. 3, pp. 99-104.
M. J. Buck, et al., "ChIP-chip: considerations for the design, analysis, and application of genome-wide chromatin immunoprecipitation experiments", Genomics, Mar. 1, 2004, vol. 83, No. 3, pp. 349-360.

\* cited by examiner

SEQUENCE LISTING

```
<160> NUMBER OF SEQ ID NOS: 15

<210> SEQ ID NO 1
<211> LENGTH: 19
<212> TYPE: DNA
<213> ORGANISM: Mus musculus

<400> SEQUENCE: 1
tagggttagg gttagggtt                                                  19

<210> SEQ ID NO 2
<211> LENGTH: 930
<212> TYPE: PRT
<213> ORGANISM: Artificial Sequence
<220> FEATURE:
<223> OTHER INFORMATION: Fusion protein 3xFN-Tel-TAL

<400> SEQUENCE: 2

Met Asp Tyr Lys Asp His Asp Gly Asp Tyr Lys Asp His Asp Ile Asp
1               5                   10                  15
```

-continued

```
Tyr Lys Asp Asp Asp Lys Leu Ala Ala Gly Arg Ala Thr Met Gly
         20              25                  30
Lys Pro Ile Pro Asn Pro Leu Leu Gly Leu Asp Ser Thr Gly Gly Met
         35              40                  45
Ala Pro Lys Lys Lys Arg Lys Val Asp Gly Val Asp Leu Arg Thr
 50                  55                  60
Leu Gly Tyr Ser Gln Gln Gln Gln Glu Lys Ile Lys Pro Lys Val Arg
 65              70                  75                  80
Ser Thr Val Ala Gln His His Glu Ala Leu Val Gly His Gly Phe Thr
                 85                  90                  95
His Ala His Ile Val Ala Leu Ser Gln His Pro Ala Ala Leu Gly Thr
                100                 105                 110
Val Ala Val Lys Tyr Gln Asp Met Ile Ala Ala Leu Pro Glu Ala Thr
                115                 120                 125
His Glu Ala Ile Val Gly Val Gly Lys Gln Trp Ser Gly Ala Arg Ala
130                 135                 140
Leu Glu Ala Leu Leu Thr Val Ala Gly Glu Leu Arg Gly Pro Pro Leu
145                 150                 155                 160
Gln Leu Asp Thr Gly Gln Leu Leu Lys Ile Ala Lys Arg Gly Gly Val
                165                 170                 175
Thr Ala Val Glu Ala Val His Ala Trp Arg Asn Ala Leu Thr Gly Ala
                180                 185                 190
Pro Leu Asn Leu Thr Pro Glu Gln Val Val Ala Ile Ala Ser Asn Ile
                195                 200                 205
Gly Gly Lys Gln Ala Leu Glu Thr Val Gln Arg Leu Leu Pro Val Leu
210                 215                 220
Cys Gln Ala His Gly Leu Thr Pro Glu Gln Val Val Ala Ile Ala Ser
225                 230                 235                 240
Asn Asn Gly Gly Lys Gln Ala Leu Glu Thr Val Gln Arg Leu Leu Pro
                245                 250                 255
Val Leu Cys Gln Ala His Gly Leu Thr Pro Glu Gln Val Val Ala Ile
                260                 265                 270
Ala Ser Asn Asn Gly Gly Lys Gln Ala Leu Glu Thr Val Gln Arg Leu
                275                 280                 285
Leu Pro Val Leu Cys Gln Ala His Gly Leu Thr Pro Glu Gln Val Val
290                 295                 300
Ala Ile Ala Ser Asn Asn Gly Gly Lys Gln Ala Leu Glu Thr Val Gln
305                 310                 315                 320
Arg Leu Leu Pro Val Leu Cys Gln Ala His Gly Leu Thr Pro Glu Gln
                325                 330                 335
Val Val Ala Ile Ala Ser Asn Gly Gly Gly Lys Gln Ala Leu Glu Thr
                340                 345                 350
Val Gln Arg Leu Leu Pro Val Leu Cys Gln Ala His Gly Leu Thr Pro
                355                 360                 365
Glu Gln Val Val Ala Ile Ala Ser Asn Gly Gly Gly Lys Gln Ala Leu
                370                 375                 380
Glu Thr Val Gln Arg Leu Leu Pro Val Leu Cys Gln Ala His Gly Leu
385                 390                 395                 400
Thr Pro Glu Gln Val Val Ala Ile Ala Ser Asn Ile Gly Gly Lys Gln
                405                 410                 415
Ala Leu Glu Thr Val Gln Arg Leu Leu Pro Val Leu Cys Gln Ala His
                420                 425                 430
```

```
Gly Leu Thr Pro Glu Gln Val Ala Ile Ala Ser Asn Asn Gly Gly
        435                 440                 445

Lys Gln Ala Leu Glu Thr Val Gln Arg Leu Leu Pro Val Leu Cys Gln
        450                 455                 460

Ala His Gly Leu Thr Pro Glu Gln Val Ala Ile Ala Ser Asn Asn
465                 470                 475                 480

Gly Gly Lys Gln Ala Leu Glu Thr Val Gln Arg Leu Leu Pro Val Leu
                485                 490                 495

Cys Gln Ala His Gly Leu Thr Pro Glu Gln Val Val Ala Ile Ala Ser
                500                 505                 510

Asn Asn Gly Gly Lys Gln Ala Leu Glu Thr Val Gln Arg Leu Leu Pro
        515                 520                 525

Val Leu Cys Gln Ala His Gly Leu Thr Pro Glu Gln Val Val Ala Ile
        530                 535                 540

Ala Ser Asn Gly Gly Gly Lys Gln Ala Leu Glu Thr Val Gln Arg Leu
545                 550                 555                 560

Leu Pro Val Leu Cys Gln Ala His Gly Leu Thr Pro Glu Gln Val Val
                565                 570                 575

Ala Ile Ala Ser Asn Gly Gly Lys Gln Ala Leu Glu Thr Val Gln
                580                 585                 590

Arg Leu Leu Pro Val Leu Cys Gln Ala His Gly Leu Thr Pro Glu Gln
        595                 600                 605

Val Val Ala Ile Ala Ser Asn Ile Gly Gly Lys Gln Ala Leu Glu Thr
        610                 615                 620

Val Gln Arg Leu Leu Pro Val Leu Cys Gln Ala His Gly Leu Thr Pro
625                 630                 635                 640

Glu Gln Val Val Ala Ile Ala Ser Asn Asn Gly Gly Lys Gln Ala Leu
                645                 650                 655

Glu Thr Val Gln Arg Leu Leu Pro Val Leu Cys Gln Ala His Gly Leu
                660                 665                 670

Thr Pro Glu Gln Val Val Ala Ile Ala Ser Asn Asn Gly Gly Lys Gln
        675                 680                 685

Ala Leu Glu Thr Val Gln Arg Leu Leu Pro Val Leu Cys Gln Ala His
        690                 695                 700

Gly Leu Thr Pro Glu Gln Val Ala Ile Ala Ser Asn Asn Gly Gly
705                 710                 715                 720

Lys Gln Ala Leu Glu Thr Val Gln Arg Leu Leu Pro Val Leu Cys Gln
                725                 730                 735

Ala His Gly Leu Thr Pro Glu Gln Val Ala Ile Ala Ser Asn Gly
                740                 745                 750

Gly Gly Lys Gln Ala Leu Glu Thr Val Gln Arg Leu Leu Pro Val Leu
        755                 760                 765

Cys Gln Ala His Gly Leu Thr Pro Gln Val Val Ala Ile Ala Ser
        770                 775                 780

Asn Gly Gly Gly Arg Pro Ala Leu Glu Ser Ile Val Ala Gln Leu Ser
785                 790                 795                 800

Arg Pro Asp Pro Ala Leu Ala Ala Leu Thr Asn Asp His Leu Val Ala
                805                 810                 815

Leu Ala Cys Leu Gly Gly Arg Pro Ala Leu Asp Ala Val Lys Lys Gly
                820                 825                 830

Leu Pro His Ala Pro Ala Leu Ile Lys Arg Thr Asn Arg Arg Ile Pro
        835                 840                 845
```

```
Glu Arg Thr Ser His Arg Val Ala Asp His Ala Gln Val Val Arg Val
850                 855                 860

Leu Gly Phe Phe Gln Cys His Ser His Pro Ala Gln Ala Phe Asp Asp
865                 870                 875                 880

Ala Met Thr Gln Phe Gly Met Ser Arg His Gly Leu Leu Gln Leu Phe
                885                 890                 895

Arg Arg Val Gly Val Thr Glu Leu Glu Ala Arg Ser Gly Thr Leu Pro
                900                 905                 910

Pro Ala Ser Gln Arg Trp Asp Arg Ile Leu Gln Gly Ser Arg Leu Ile
            915                 920                 925

His Arg
    930
```

<210> SEQ ID NO 3
<211> LENGTH: 23
<212> TYPE: DNA
<213> ORGANISM: Artificial Sequence
<220> FEATURE:
<223> OTHER INFORMATION: Primer Sequence

<400> SEQUENCE: 3
ccggcgcccc gcggctgaca gag                                       23

<210> SEQ ID NO 4
<211> LENGTH: 24
<212> TYPE: DNA
<213> ORGANISM: Artificial Sequence
<220> FEATURE:
<223> OTHER INFORMATION: Primer Sequence

<400> SEQUENCE: 4
gctgtgggtt ctggtctttt gttc                                      24

<210> SEQ ID NO 5
<211> LENGTH: 19
<212> TYPE: DNA
<213> ORGANISM: Artificial Sequence
<220> FEATURE:
<223> OTHER INFORMATION: Primer Sequence

<400> SEQUENCE: 5
gcggcagcgg agtcctaag                                            19

<210> SEQ ID NO 6
<211> LENGTH: 13
<212> TYPE: DNA
<213> ORGANISM: Homo sapiens

<400> SEQUENCE: 6
ttattccctg aca                                                  13

<210> SEQ ID NO 7
<211> LENGTH: 13
<212> TYPE: DNA
<213> ORGANISM: Homo sapiens

<400> SEQUENCE: 7
tcttacttat aac                                                  13

<210> SEQ ID NO 8
<211> LENGTH: 13
<212> TYPE: DNA
<213> ORGANISM: Homo sapiens

<400> SEQUENCE: 8
accactcact ata                                                          13

<210> SEQ ID NO 9
<211> LENGTH: 25
<212> TYPE: DNA
<213> ORGANISM: Artificial Sequence
<220> FEATURE:
<223> OTHER INFORMATION: Primer Sequence

<400> SEQUENCE: 9
attggtcgct agaaacccat ttatt                                             25

<210> SEQ ID NO 10
<211> LENGTH: 25
<212> TYPE: DNA
<213> ORGANISM: Artificial Sequence
<220> FEATURE:
<223> OTHER INFORMATION: Primer Sequence

<400> SEQUENCE: 10
ctgccttgac aactcctgat acttt                                             25

<210> SEQ ID NO 11
<211> LENGTH: 23
<212> TYPE: DNA
<213> ORGANISM: Homo sapiens

<400> SEQUENCE: 11 ccggggcgc tgggctgtcc cgg                                                23

<210> SEQ ID NO 12
<211> LENGTH: 60
<212> TYPE: DNA
<213> ORGANISM: Artificial Sequence
<220> FEATURE:
<223> OTHER INFORMATION: Oligonucleotide

<400> SEQUENCE: 12
tttcttggct ttatatatct tgtggaaagg acgaaacacc gcggggcgc tgggctgtcc        60

<210> SEQ ID NO 13
<211> LENGTH: 60
<212> TYPE: DNA
<213> ORGANISM: Artificial Sequence
<220> FEATURE:
<223> OTHER INFORMATION: Oligonucleotide

<400> SEQUENCE: 13
gactagcctt attttaactt gctatttcta gctctaaaac ggacagccca gcgccccgc        60

<210> SEQ ID NO 14
<211> LENGTH: 22
<212> TYPE: DNA
<213> ORGANISM: Artificial Sequence
<220> FEATURE:
<223> OTHER INFORMATION: Primer Sequence

<400> SEQUENCE: 14
cgcctgcgtt cgggagatat ac                                                22

<210> SEQ ID NO 15
<211> LENGTH: 22
<212> TYPE: DNA

```
<213> ORGANISM: Artificial Sequence
<220> FEATURE:
<223> OTHER INFORMATION: Primer Sequence

<400> SEQUENCE: 15
ctgtcctctc actccgcctt gt                                              22
```

//  METHOD FOR ISOLATING SPECIFIC GENOMIC REGIONS WITH USE OF MOLECULE CAPABLE OF SPECIFICALLY BINDING TO ENDOGENOUS DNA SEQUENCE

TECHNICAL FIELD

The present invention relates to a method for isolating a specific genomic region with the use of a molecule capable of specifically binding to an endogenous DNA sequence, and in particular, to a method for isolating a specific genomic region with the use of a molecule capable of specifically binding to an endogenous DNA sequence, while maintaining the interaction of the specific genomic region and molecules interacting therewith.

BACKGROUND ART

Biochemical and molecular biological analysis of chromatin domains is critical for understanding of the molecular mechanisms of genome functions. However, the biochemical nature of chromatin domains is poorly understood. This is because sampling methods that can be used for biochemical and molecular biological analysis of chromatin domains are limited.

The biochemical and molecular biological analysis of chromatin domains requires a sample retaining the interaction of genomic DNA and molecules interacting therewith. Known examples of the method for isolating a specific genomic region while maintaining the interaction of the specific genomic region and molecules interacting therewith include the following.

(i) Chromatin Immunoprecipitation

Chromatin immunoprecipitation (hereinafter referred to as "ChIP") is a method which involves immunoprecipitation of a specific genomic region with an antibody against a known DNA-binding protein to isolate the region concerned (see Non Patent Literature 1 and 2). Therefore, there is a limitation that ChIP cannot be used without the information regarding DNA-binding proteins. In addition, ChIP has difficulty in isolating a single specific genomic region. This is because DNA-binding proteins generally bind to a plurality of regions in genomic DNA and thus the resulting immunoprecipitate contains various genomic regions. Further, ChIP cannot isolate a genomic region to which known DNA-binding proteins do not bind.

(ii) Chromosome Conformation Capture (Hereinafter Referred to as "3C")

3C or its derivatives can identify a genomic region(s) interacting with a specific genomic region(s) (see Non Patent Literature 3 to 5). However, 3C is likely to detect unphysiological interaction because 3C requires an enzymatic reaction with restriction enzymes or DNA ligases in the presence of crosslinks, which is not an optimal condition for the enzymatic reaction. In addition, the presence of crosslinks causes incomplete digestion by restriction enzymes, and thus neighboring regions of the target genomic region are unavoidably amplified by PCR, resulting in a very high background, which makes it difficult to detect unidentified interactions.

(iii) Fluorescence In Situ Hybridization (Hereinafter Referred to as "FISH")

FISH alone or in combination with immunofluorescence can detect the interaction of a specific genomic region with other genomic regions, RNAs and proteins. However, this method has a low resolution and cannot detect any interaction with unidentified molecules.

(iv) Proteomics of Isolated Chromatin Segments (Hereinafter Referred to as "PICh")

PICh is a method for isolating a specific genomic region with the use of a specific nucleic acid probe, and is reported to be capable of isolating telomeric regions having multiple repeats of a sequence complementary to the probe (see Non Patent Literature 6). This method requires annealing of a nucleic acid probe and a target genomic region in the presence of crosslinks, and the feasibility of the isolation of a single- or low-copy specific genomic region has not been shown.

(v) Method of Non Patent Literature 7

Non Patent Literature 7 describes an attempt to isolate a specific genomic region by affinity purification. In this attempt, the cells used are yeast cells and higher eukaryotic cells are yet to be tested. In addition, the Cre-loxP system is used for excision of the specific genomic region, but this procedure has a risk of altering chromatin structures. Further, crosslinking treatment with formaldehyde cannot be used, and therefore interacting molecules, such as proteins and DNAs, may dissociate from the specific genomic region during a purification process.

(vi) iChIP

This is a method that the present inventors previously developed (see Patent Literature 1, and Non Patent Literature 8 and 9). In order to isolate a specific genomic region retaining a physiological chromatin structure, the following procedures are performed.

(1) A recognition sequence of an exogenous DNA-binding molecule is inserted into the vicinity of a target genomic region in cells to be analyzed.

(2) The cells to be analyzed are made to express a fusion molecule of a DNA-binding domain of the exogenous DNA-binding molecule and a tag recognizable by existing antibodies or other proteins.

(3) If, needed, the cells are subjected to crosslinking treatment with formaldehyde etc. This procedure allows the formation of crosslinks between the target genomic region and its interacting molecules such as proteins, RNAs and DNAs. In addition, crosslinks between the tagged exogenous DNA-binding molecule and the inserted recognition sequence are also formed.

(4) Subsequently, the cells are disrupted, and the crosslinked DNA is fragmented by treatment with a deoxyribonuclease (s) such as a restriction enzyme or by ultrasonication.

(5) A complex containing the tagged exogenous DNA-binding molecule is precipitated with a carrier on which an antibody, a protein or others that recognize the tag is immobilized.

(6) Molecules interacting with the target genomic region in the precipitated complex are analyzed.

The problems of iChIP are the following: time and effort are required to insert the recognition sequence of the exogenous DNA-binding molecule into the vicinity of the target genomic region of the cells to be analyzed; and the possibility that the insertion of the recognition sequence influences the interaction of interest cannot be eliminated.

CITATION LIST

Patent Literature

Patent Literature 1: WO 2011/021684

Non Patent Literature

Non Patent Literature 1:
Solomon, M. J., Larsen, P. L., Varshaysky, A., Mapping protein-DNA interactions in vivo with formaldehyde: evidence that histone H4 is retained on a highly transcribed gene. Cell (1988) 53, 937-947

Non Patent Literature 2:
Solomon, M. J., Varshaysky, A., Formaldehyde-mediated DNA-protein crosslinking: a probe for in vivo chromatin structures. Proc. Natl. Acad. Sci. USA (1985) 82, 6470-6474

Non Patent Literature 3:
Dekker, J., Rippe, K., Dekker, M., and Kleckner, N. Capturing chromosome conformation. Science (2002) 295, 1306-1311

Non Patent Literature 4:
Simonis, M., Klous, P., Splinter, E., Moshkin, Y., Willemsen, R., de Wit, E., van Steensel, B., and de Laat, W. Nuclear organization of active and inactive chromatin domains uncovered by chromosome conformation capture-on-chip (4C). Nat. Genet. (2006) 38, 1348-1354

Non Patent Literature 5:
Simonis, M., Kooren, J., and de Laat, W. An evaluation of 3C-based methods to capture DNA interactions. Nat. Methods (2007) 4, 895-901

Non Patent Literature 6:
Dejardin, J., and Kingston, R. E. Purification of proteins associated with specific genomic loci. Cell (2009) 136, 175-186

Non Patent Literature 7:
Griesenbeck, J., Boeger, H., Strattan, J. S., and Kornberg, R. D. Affinity purification of specific chromatin segments from chromosomal loci in yeast. Mol. Cell Biol. (2003) 23, 9275-9282

Non Patent Literature 8:
Hoshino, A., and Fujii, H. Insertional chromatin immunoprecipitation: a method for isolating specific genomic regions. J. Biosci. Bioeng. (2009) 108, 446-449

Non Patent Literature 9:
Fujita, H., and Fujii, H. Direct identification of insulator components by insertional chromatin immunoprecipitation. PLoS One (2011) 6, e26109

SUMMARY OF INVENTION

Technical Problem

An object of the present invention is to provide a method for specifically isolating any genomic region while maintaining the interaction of the genomic region and molecules interacting therewith, the method being characterized by using an endogenous DNA sequence present inside or in the vicinity of a target genomic region in cells to be analyzed and by having no need of inserting a recognition sequence of an exogenous DNA-binding molecule into the vicinity of the target genomic region in the cells to be analyzed.

Solution to Problem

The present invention includes the following to achieve the above-mentioned object.
(1) A method for isolating a specific genomic region while maintaining the interaction of the specific genomic region and molecules interacting therewith, the method comprising the following steps (A) and (B):
(A) fragmenting genomic DNA in a state where the interaction of the genomic DNA and molecules interacting therewith is maintained, and
(B) bringing genomic DNA into contact with an exogenous molecule capable of binding to a specific endogenous DNA sequence in the genomic DNA.
(2) The method according to the above (1), further comprising the step of (C) performing a treatment for maintaining the interaction of genomic DNA and molecules interacting therewith.
(3) The method according to the above (1) or (2), wherein the exogenous molecule is an exogenous DNA-binding protein, an exogenous nucleic acid or an exogenous protein-nucleic acid complex.
(4) The method according to the above (1) or (2), wherein the exogenous molecule is a zinc finger protein, a TAL effector protein, or a complex of an inactive Cas9 protein and a guide RNA (gRNA).
(5) The method according to any one of the above (1) to (4), wherein the method comprises the following steps 1 to 3:
step 1: bringing genomic DNA in cells into contact with the exogenous molecule,
step 2: fragmenting the genomic DNA in the cells in a state where the interaction of the genomic DNA and molecules interacting therewith is maintained, and
step 3: allowing a genomic DNA fragment bound to the exogenous molecule to form a complex with a molecule capable of specifically binding to the exogenous molecule, and then harvesting the complex.
(6) The method according to the above (5), wherein the exogenous molecule is a fusion molecule containing one or more kinds of tag sequences.
(7) The method according to the above (5) or (6), wherein the exogenous molecule is a fusion molecule having a nuclear localization signal(s).
(8) The method according to any one of the above (5) to (7), wherein, in step 1, a gene(s) encoding the exogenous molecule is introduced into the cells to be analyzed for expression of the gene in the cells.
(9) The method according to any one of the above (1) to (4), wherein the method comprises the following steps I to III:
step I: fragmenting genomic DNA in a state where the interaction of the genomic DNA and molecules interacting therewith is maintained,
step II: bringing the fragmented genomic DNA into contact with the exogenous molecule, and
step III: harvesting a genomic DNA fragment bound to the exogenous molecule.
(10) The method according to the above (9), wherein, in step II, the fragmented genomic DNA is brought into contact with the exogenous molecule immobilized on a carrier.
(11) The method according to the above (9), wherein, in step II, the exogenous molecule is brought into contact with the fragmented genomic DNA and subsequently immobilized onto a carrier.

Advantageous Effects of Invention

According to the present invention, with the use of an endogenous DNA sequence present inside or in the vicinity of a target genomic region in cells to be analyzed, any genomic region can be specifically isolated in a state where the interaction of the genomic region and molecules interacting therewith is maintained. The method of the present invention for isolating a specific genomic region uses an endogenous DNA sequence present inside or in the vicinity of a target genomic region in cells to be analyzed and does not need the insertion of a recognition sequence of an exogenous DNA-binding molecule, and therefore can eliminate the influence of an insertion sequence on the interaction of interest. Consequently, the genomic region isolated by the method of the present invention is very useful as a sample for the analysis of the molecular mechanisms of genome functions.

DESCRIPTION OF EMBODIMENTS

<Method for Isolating Specific Genomic Regions>

Figure 1:
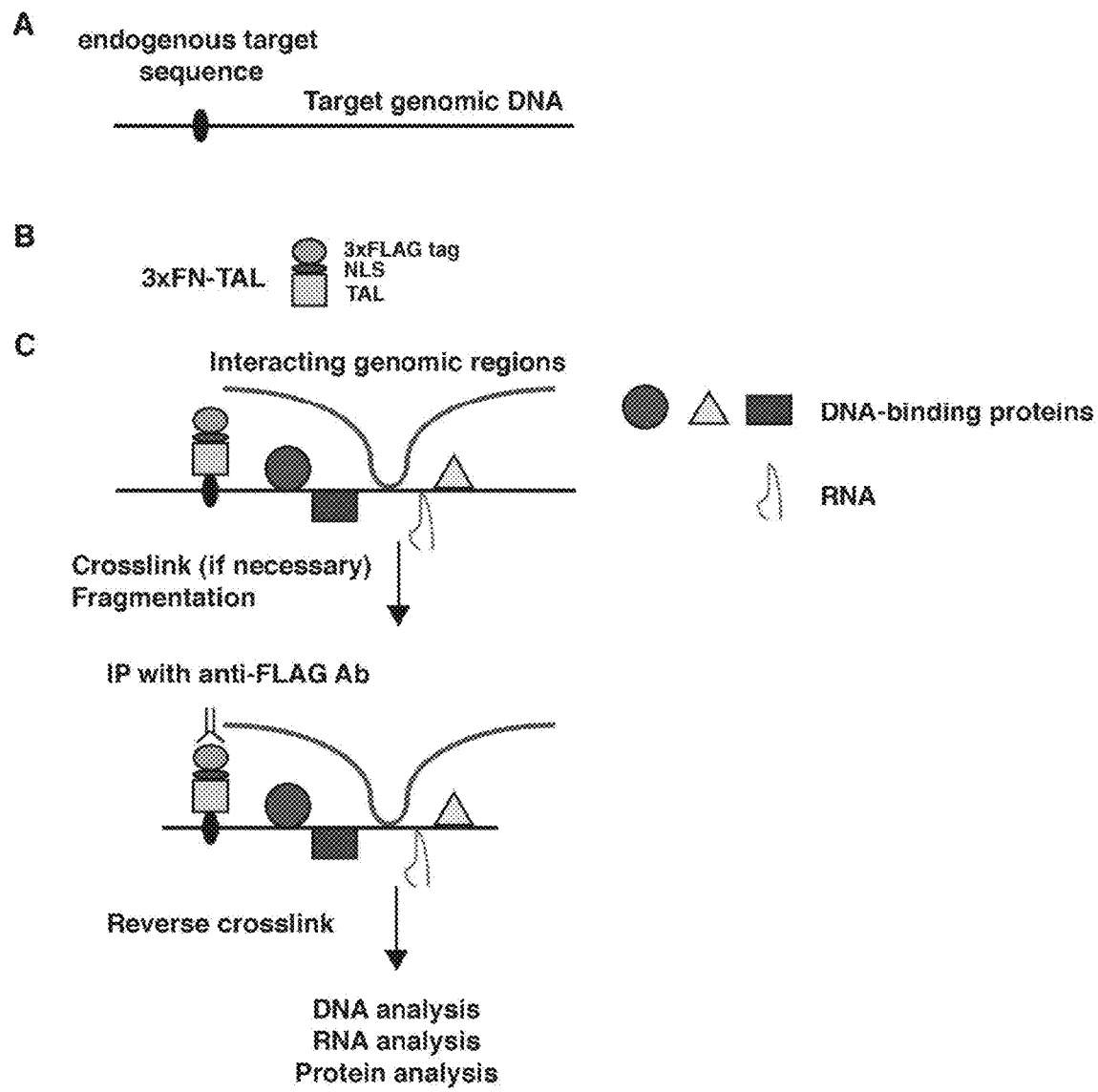
FIG. 1 shows the first embodiment of the method of the present invention for isolating a specific genomic region.

The method of the present invention for isolating a specific genomic region (hereinafter referred to as "the method of the present invention") comprises the following steps (A) and (B):

(A) fragmenting genomic DNA in a state where the interaction of the genomic DNA and molecules interacting therewith is maintained, and (B) bringing genomic DNA into contact with an exogenous molecule capable of binding to a specific endogenous DNA sequence in the genomic DNA. The order of steps (A) and (B) is not limited, and step (A) may precede or follow step (B).

The method of the present invention preferably further comprises the following step (C):

(C) performing a treatment for maintaining the interaction of genomic DNA and molecules interacting therewith.

Step (C) preferably precedes step (A).

The exogenous molecule is not particularly limited as long as it is an exogenous molecule capable of binding to a specific endogenous DNA sequence in genomic DNA. For example, exogenous DNA-binding proteins, exogenous nucleic acids, exogenous protein-nucleic acid complexes, etc. can preferably be used. The exogenous DNA-binding protein is preferably a protein of which the amino acid sequence can be designed in association with the nucleotide sequence of a target DNA. Examples of such an exogenous DNA-binding protein include zinc finger proteins and TAL effector proteins. Examples of the exogenous nucleic acid include DNA aptamers and RNA aptamers. Examples of the exogenous protein-nucleic acid complex include a complex of an inactive Cas9 protein and a guide RNA (gRNA).

It is known that zinc finger proteins can be modified so as to recognize the nucleotide sequence of a specific DNA (for example, see Beerli et al., (2002) Nature Biotechnol. 20: 135-141; Pabo et al., (2001) Ann. Rev. Biochem. 70: 313-340; Isalan et al., (2001) Nature Biotechnol. 19: 656-660; Segal et al., (2001) Curr. Opin. Biotechnol. 12: 632-637; and Choo et al., (2000) Curr. Opin. Struct. Biol. 10: 411-416). Such modification can impart zinc finger proteins with a novel binding specificity that native zinc finger proteins do not have. The modification method is not particularly limited, and for example, a method involving combining zinc finger modules each having known specificity can be employed.

The specificity can be selected by phage display, two-hybrid system or the like, and such selection methods are disclosed in U.S. Pat. Nos. 5,789,538; 5,925,523; 6,007,988; 6,013,453; 6,410,248; 6,140,466; 6,200,759; 6,242,568; WO 98/37186; WO 98/53057; WO 00/27878; WO 01/88197; Great Britain Patent No. 2,338,237; etc.

TAL effector proteins are proteins isolated from *Xanthomonas* bacteria, which are known as plant pathogens. The DNA-binding domain of TAL effector proteins has an almost complete tandem repeat structure in which each repeat unit consists of approximately 34 amino acids. The 12th and 13th amino acids of each repeat unit are hypervariable and called the repeat variable diresidue (RVD). The RVD determines the DNA base-recognition specificity of each repeat unit. For the preparation of a TAL effector protein which recognizes a specific nucleotide sequence, repeat units each having a desired RVD are appropriately combined (see Moscou and Bogdanove, (2009) Science 326: 1501; Boch et al., (2009) Science 326: 1509-1512; and Miller et al., (2011) Nat. Biotechnol., 29: 143-148).

The exogenous nucleic acid can be obtained, for example, by affinity purification of a molecular species capable of binding to a target genomic DNA sequence from a random nucleic acid sequence library, followed by enrichment and selection by use of PCR etc. Into such a selected nucleic acid, a suitable mutation may be introduced to increase the affinity for the target genomic DNA sequence.

The exogenous protein-nucleic acid complex is preferably a complex of an inactive Cas9 protein and a gRNA. The Cas9 protein is a bacterial and archaeal enzyme which cleaves a sequence specific to a gRNA in an RNA-guided manner (CRISPR system). The inactive Cas9 protein is a Cas9 mutant which lacks in DNA cleavage activity but is capable of binding to a DNA sequence complementary to a gRNA in an RNA-guided manner (Jinek et al., (2012) Science, 337: 816-821). For this reason, a complex of inactive Cas9 and an RNA containing a sequence complementary to a target DNA sequence is suitable as an exogenous molecule used for the method of the present invention.

The specific endogenous DNA sequence in genomic DNA as the binding site of the exogenous molecule can be selected from DNA sequences which are present inside or in the vicinity of a genomic region to be isolated. It is preferable to select a DNA sequence which is present only inside or in the vicinity of the genomic region to be isolated and is not present in any other region of the genomic DNA, but a DNA sequence which is present inside or in the vicinity of the genomic region to be isolated and is infrequently present in the other regions of the genomic DNA may also be selected.

In step (B), the method for bringing genomic DNA into contact with the exogenous molecule is not particularly limited. Such contact may be effected in the nuclei of the cells. Alternatively, genomic DNA in a state where the interaction of the genomic DNA and molecules interacting therewith is maintained may be extracted from the cells before the contact. In addition, a plurality of endogenous DNA sequences which are present inside or in the vicinity of the genomic region to be isolated may be selected and brought into contact with a plurality of exogenous molecules which bind to the corresponding DNA sequences. After the contact with a plurality of exogenous molecules, the implementation of successive purification allows more specific isolation of the target genomic region.

The fragmentation of genomic DNA in step (A) is intended to produce a genomic DNA fragment of an appropriate size which can contain a genomic region of interest. Examples of the method for the fragmentation of genomic DNA include digestion of genomic DNA with a restriction enzyme(s), partial degradation (partial cleavage) of genomic DNA with a deoxyribonuclease(s) (endonuclease(s)), and physical cleavage of genomic DNA by ultrasonication.

In the case where a restriction enzyme(s) is used, it is preferable to select a restriction enzyme(s) whose cleavage site is absent within the genomic region to be isolated and located as close as possible to the genomic region of interest.

In the case where a deoxyribonuclease(s) (endonuclease(s)) is used, it is preferable to determine in advance the reaction conditions for production of a fragment slightly larger than the size of the genomic region to be isolated.

In the case of ultrasonication, it is preferable to determine in advance the treatment conditions for production of a fragment slightly larger than the size of the genomic region to be isolated.

During the fragmentation of genomic DNA, it is preferable that the interaction of the genomic DNA and molecules interacting therewith is maintained. Therefore, it is preferable that, before the fragmentation of genomic DNA, a treatment for maintaining the interaction of the genomic DNA and molecules interacting therewith (step (C)) is performed as needed. The treatment for maintaining the interaction is not particularly limited, but preferably, the interaction maintained as a result of the treatment can be eliminated as needed so that the interacting molecules can be separated and purified for subsequent analysis. Preferable examples of the treatment include crosslinking. Preferable examples of an agent used for the crosslinking include formaldehyde.

First Embodiment

The method of the present invention comprises steps 1 to 3 shown below. The method of the present invention enables isolation of a specific genomic region in a state where the interaction of the specific genomic region and molecules interacting therewith is maintained. As long as a specific genomic region can be isolated in a state where the interaction is maintained, the method may comprise a step(s) other than steps 1 to 3, and the details of the step(s) are not limited. In the first embodiment, the cells to be analyzed are preferably viable cells.

Step 1: bringing genomic DNA in cells into contact with an exogenous molecule capable of binding to a specific endogenous DNA sequence in the genomic DNA.

Step 2: fragmenting the genomic DNA in the cells in a state where the interaction of the genomic DNA and molecules interacting therewith is maintained.

Step 3: allowing a genomic DNA fragment bound to the exogenous molecule to form a complex with a molecule capable of specifically binding to the exogenous molecule, and then harvesting the complex.

Hereinafter, the method of the present invention will be described in detail in the order of the steps.

(1) Step 1

Step 1 is a step of bringing genomic DNA in cells into contact with an exogenous molecule capable of binding to a specific endogenous DNA sequence in the genomic DNA.

In the first embodiment of the method of the present invention, the exogenous molecule is preferably a fusion molecule containing one or more kinds of tag sequences. In the case where the exogenous molecule contains a tag sequence(s), molecules capable of specifically binding to the exogenous molecule are easily available. The tag sequence is not particularly limited and can be selected as appropriate from known tag sequences. Specific examples of the tag sequence include a histidine tag, a FLAG tag, a Strep tag, a calmodulin-binding peptide, a GST tag, an MBP tag, a Halo tag and an HA tag.

The fusion molecule of the exogenous molecule and a tag sequence may comprise two or more kinds of tag sequences. The two or more kinds of tag sequences may be directly linked, or linked via a protease recognition sequence and/or a spacer sequence. In the case where such a structure is employed, a genomic region bound to the fusion molecule can be purified in two or more steps, and thus the background due to nonspecific binding can be significantly reduced and the efficiency of specific isolation of specific genomic regions is significantly improved.

The protease recognition sequence for linking the tag sequences can be selected as appropriate from the recognition sequences of proteases usually used for removal of tag sequences. Known as the protease used for removal of tag sequences are, for example, tobacco etch virus (TEV) protease, human rhinovirus (HRV) protease, enterokinase (EK), thrombin (Tb) and Factor Xa.

In the case where the cells to be analyzed are eukaryotic cells, the fusion molecule preferably contains a nuclear localization signal(s). The fusion molecule having a nuclear localization signal(s) can enter into the nucleus and come into contact with genomic DNA. The nuclear localization signal can be selected as appropriate from known nuclear localization signals. Specific examples of the nuclear localization signal include the nuclear localization signal of SV40 T antigen, the nuclear localization signal of c-Myc, the nuclear localization signal of p53, and the nuclear localization signal of NF-κB p50 Alternatively, the fusion molecule may have the amino acid sequence of a cell-permeable motif (protein transduction domain).

In the case where the exogenous molecule is a protein, the exogenous molecule can be produced, for example, as a recombinant protein by known recombinant techniques, that is, by inserting a DNA encoding the desired exogenous protein into a known expression vector, introducing the resulting expression vector into appropriate host cells for expression of the protein, and purifying the expressed protein by a known method. In the case where the exogenous protein is a fusion protein, DNAs each encoding a different constituent protein of the fusion protein are appropriately fused, and the resulting fusion DNA is inserted into an expression vector in the course of the production of the exogenous molecule.

In the case where the exogenous molecule is a nucleic acid, the nucleic acid can be produced by, for example, known methods such as chemical synthesis, PCR, in vitro transcription, reverse transcription, transcription from integrated genes in cells, etc. In the case where the exogenous nucleic acid is a fusion molecule, it can be produced by a known chemical synthesis.

The method for bringing genomic DNA in cells into contact with the exogenous molecule is not particularly limited. For example, an exogenous protein or nucleic acid obtained by known recombinant techniques etc. as described above, is introduced by microinjection, electroporation, lipofection, etc. into the cells to be analyzed. Alternatively, a fusion molecule having the amino acid sequence of a cell-permeable motif (protein transduction domain) as mentioned above may be used as the exogenous molecule and directly introduced into the cells to be analyzed. Alternatively, apart from the exogenous molecule, a protein transduction domain fused to an amino acid sequence capable of binding to the exogenous molecule may be prepared and then introduced as a mixture with the exogenous molecule into the cells to be analyzed.

Another option is to express the exogenous molecule in cells. To this end, the cells to be analyzed are used as a host cell, and an expression vector that can express the exogenous molecule in the cells is prepared and then introduced into the cells. In the case where the host is a prokaryotic cell, the expressed exogenous molecule can come into contact with genomic DNA in the cytoplasm. In the case where the host is a eukaryotic cell, a fusion molecule having a nuclear localization signal(s) is used as the exogenous molecule to be expressed, so that the expressed exogenous molecule can enter into the nucleus from the cytoplasm and come into contact with genomic DNA. Alternatively, a transgenic organism created by introducing an expressible form of a gene encoding the exogenous molecule can also be used to achieve the contact of the exogenous molecule with genomic DNA in cells.

The exogenous molecule in contact with the genomic DNA can bind to a target endogenous DNA sequence in the genomic DNA.

(2) Step 2

Step 2 is a step of fragmenting the genomic DNA in the cells in a state where the interaction of the genomic DNA and molecules interacting therewith is maintained. It is preferable that step 2 is preceded by a step of performing a treatment for maintaining the interaction of the genomic DNA and molecules interacting therewith, but such a treatment step can be skipped.

With the genomic DNA, DNA-binding proteins such as transcription factors, nucleic acids such as DNAs and RNAs, other molecules, etc. are interacting depending on the cell cycle status, extracellular stimulation, etc. Therefore, it is preferable that the timing for the treatment for maintaining the interaction or for fragmenting the genomic DNA is selected as appropriate for a particular analytical purpose. Before such a treatment, the cells may be stimulated if needed. For efficient fragmentation, it is preferable that cell lysis, cell disruption or chromatin fraction extraction is performed according to a known method before fragmentation.

Step 2 produces a DNA fragment to which the exogenous molecule is bound, and a DNA fragment (s) to which the exogenous molecule is not bound.

(3) Step 3

Step 3 is a step of allowing a DNA fragment bound to the exogenous molecule to form a complex with a molecule capable of specifically binding to the exogenous molecule, and then harvesting the complex. Since the exogenous molecule is bound to a specific endogenous DNA sequence present inside or in the vicinity of the genomic region to be isolated, the DNA fragment bound to the exogenous molecule is supposed to contain the desired specific genomic region. Therefore, the desired specific genomic region can be isolated by harvesting a complex formed by the binding of a molecule capable of specifically binding to the exogenous molecule.

The method used in step 3 may be any method that enables the formation of a complex of an exogenous molecule-bound DNA fragment containing the desired specific genomic region and a molecule capable of specifically binding to the exogenous molecule, and subsequent harvesting of the complex. For example, the complex can be harvested after precipitated with a carrier on which an antibody or a peptide capable of specifically binding to the exogenous molecule, a nickel ion, etc. is immobilized.

For example, in the case where the exogenous molecule is a fusion molecule having two kinds of tag sequences linked via a protease recognition sequence, the following procedures are preferable. The obtained DNA fragment is made to bind to a molecule capable of specifically binding to a first tag sequence, for formation of a first complex, and then the first complex is treated with a protease for cleavage of the protease recognition sequence. The genomic DNA-containing portion separated from the first complex is made to bind to a molecule capable of specifically binding to a second tag sequence, for formation of a second complex. Such a two-step purification can prevent undesired events, for example, enrichment of molecules as the background due to nonspecific binding to a molecule capable of specifically binding to the first tag sequence, and nonspecific binding to a carrier on which such a molecule is immobilized. As a result, the efficiency of specific isolation of specific genomic regions is significantly improved.

In the case where the exogenous molecule is not the one in which two kinds of tag sequences are linked via a protease recognition sequence, separation of the desired complex from a molecule capable of specifically binding to a tag sequence can reduce the background. Specifically, for example in the case where a FLAG tag is used as the tag sequence, addition of a FLAG peptide can separate the desired complex from an anti-FLAG antibody bound to the complex.

Hereinafter, one example of the first embodiment of the present invention will be described with reference to FIG. 1. However, the method of the present invention is not limited to this embodiment.

(1) An endogenous DNA sequence present inside or in the vicinity of the desired genomic region in cells to be analyzed as shown in FIG. 1A is determined as the binding target of an exogenous molecule.

(2) A TAL effector protein capable of specifically binding to the determined endogenous DNA sequence is designed. An expression vector for a fusion protein of the TAL effector protein, a nuclear localization signal (NLS) sequence and a tag sequence consisting of 3 repeats of a FLAG tag (3×FN-TAL, see FIG. 1B) is prepared and introduced into the cells to be analyzed so that the fusion protein can be expressed therein.

(3) If needed, the cells to be analyzed, namely the cells into which the expression vector for 3×FN-TAL has been introduced, are stimulated. If needed, in order to maintain the interaction of the genomic DNA with proteins, RNAs, DNAs and other interacting molecules in the genomic region to be isolated, the cells are subjected to crosslinking treatment with a crosslinking agent such as formaldehyde. Needless to say, 3×FN-TAL is bound to the target endogenous DNA sequence (see the top of FIG. 1C).

(4) The cells are lysed, and the genomic DNA in a state where the interaction is maintained is digested with a deoxyribonuclease(s) such as a restriction enzyme for fragmentation. Alternatively, the fragmentation may be performed by ultrasonication. This step produces a DNA fragment to which 3×FN-TAL is bound, and a DNA fragment(s) to which 3×FN-TAL is not bound.

(5) The DNA fragment to which 3×FN-TAL is bound forms a complex with an anti-FLAG antibody (immunoprecipitated complex) (see the bottom of FIG. 1C).

(6) The complex, even after isolated, retains molecules interacting with the genomic region. Therefore, after the interaction (crosslinks) is eliminated, the interacting molecules such as proteins, RNAs, DNAs and other molecules can be purified and identified.

Second Embodiment

The method of the present invention comprises steps I to III shown below. The method of the present invention enables isolation of a specific genomic region in a state where the interaction of the specific genomic region and molecules interacting therewith is maintained. As long as a specific genomic region can be isolated in a state where the interaction is maintained, the method may comprise a step(s) other than steps I to III, and the details of the step(s) are not limited. In the second embodiment, the cells to be analyzed are not limited to viable cells, and cells in a tissue specimen, etc. are also preferable.

Step I: fragmenting genomic DNA in a state where the interaction of the genomic DNA and molecules interacting therewith is maintained.

Step II: bringing the fragmented genomic DNA into contact with an exogenous molecule capable of binding to a specific endogenous DNA sequence in the genomic DNA.

Step III: harvesting a genomic DNA fragment bound to the exogenous molecule.

Hereinafter, the method of the present invention will be described in detail in the order of the steps.

(1) Step I

Step I is a step of fragmenting genomic DNA in a state where the interaction of the genomic DNA and molecules interacting therewith is maintained. In the case where viable cells are used as the cells to be analyzed, it is preferable that step I is preceded by a step of performing a treatment for maintaining the interaction of the genomic DNA and molecules interacting therewith, but such a treatment step can be skipped. In viable cells, molecules interacting with genomic DNA are supposed to vary depending on the cell cycle status, extracellular stimulation, etc. Therefore, it is preferable that the timing for the treatment for maintaining the interaction or for fragmenting genomic DNA is selected as appropriate for a particular analytical purpose. Before such a treatment, the cells may be stimulated if needed.

In the case where the cells to be analyzed are cells in a tissue specimen etc., the interaction of genomic DNA and molecules interacting therewith is supposed to be maintained. Therefore, there is usually no need for an additional treatment for maintaining the interaction.

Whichever cells are to be analyzed, it is preferable for efficient fragmentation that cell lysis, cell disruption or chromatin fraction extraction is performed according to a known method before fragmentation.

(2) Step II

Step II is a step of bringing the fragmented genomic DNA into contact with an exogenous molecule capable of binding to a specific endogenous DNA sequence in the genomic DNA. The exogenous molecule is preferably immobilized on a carrier in advance and then brought into contact with the fragmented genomic DNA prepared in step I. Alternatively, the exogenous molecule may be brought into contact with the fragmented genomic DNA and then immobilized onto a carrier. With the use of an exogenous molecule immobilized on a carrier, only a DNA fragment containing an endogenous DNA sequence to which the exogenous molecule binds can be trapped onto the carrier. The exogenous molecule can be produced by the method described in the first embodiment.

The carrier on which the exogenous molecule is immobilized is not particularly limited as long as it can immobilize a protein or a nucleic acid. Examples of the carrier include beads, magnetic beads, disks, sticks, tubes, microtiter plates, microsensor chips and microarrays all of which are made of glass, polyethylene, polypropylene, polyvinyl acetate, polyvinyl chloride, methacrylates, latex, agarose, cellulose, dextran, starch, dextrin, silica gel, porous ceramics or the like. The method for immobilizing the exogenous molecule onto the carrier can be selected as appropriate from known methods such as physical adsorption, covalent binding and crosslinking.

(3) Step III

Step III is a step of harvesting a genomic DNA fragment bound to the exogenous molecule. Since the exogenous molecule binds to a specific endogenous DNA sequence present inside or in the vicinity of the genomic region to be isolated, a genomic DNA fragment bound to the exogenous molecule is supposed to contain the desired specific genomic region. Therefore, the desired specific genomic region can be isolated by harvesting a genomic DNA fragment bound to the exogenous molecule.

The concrete procedures in steps II and III are not particularly limited. For example, a carrier on which the exogenous molecule is immobilized is packed into a column, the DNA fragment prepared in step I is passed through the column so that the desired genomic DNA region binds to the exogenous molecule, the column is washed, and subsequent elution is performed to harvest the desired genomic DNA region. In another example, the DNA fragment prepared in step I is added to a tube containing a carrier on which the exogenous molecule is immobilized, the mixture is subjected to stirring or other operations so that the desired genomic DNA region comes into contact with the exogenous molecule, the carrier is washed, and subsequent elution is performed to harvest the desired genomic DNA region.

Figure 2:
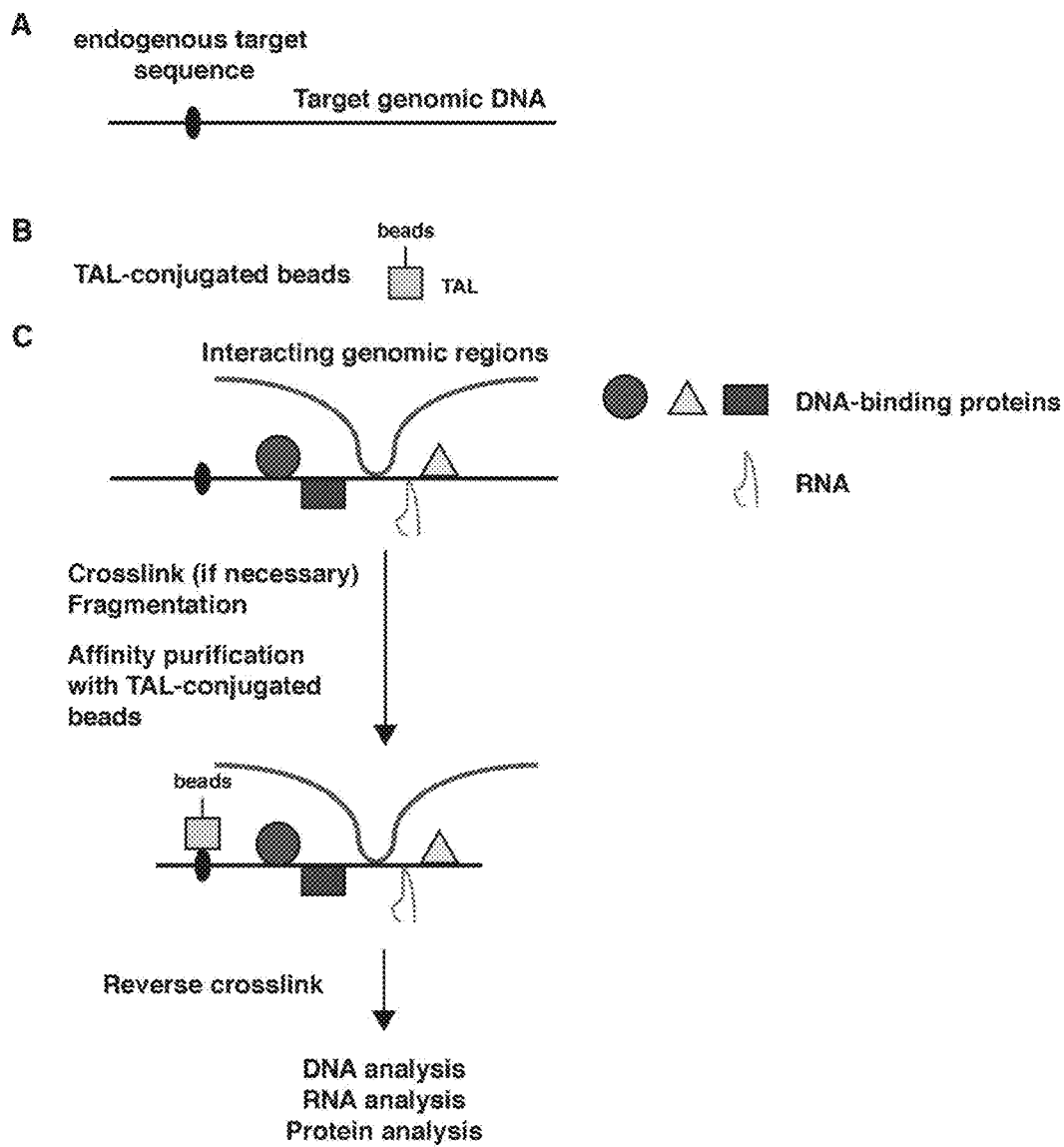
FIG. 2 shows the second embodiment of the method of the present invention for isolating a specific genomic region.

One example of the second embodiment of the present invention is shown in FIG. 2. However, the method of the present invention is not limited to this embodiment. Hereinafter, the second embodiment of the present invention will be described with reference to FIG. 2.

(1) An endogenous DNA sequence present inside or in the vicinity of the desired genomic region in cells to be analyzed as shown in FIG. 2A is determined as the binding target of an exogenous molecule.

(2) A TAL effector protein capable of specifically binding to the determined endogenous DNA sequence is designed, and a recombinant protein in which the TAL effector protein is tagged is obtained. The tag is, for example, HaloTag (registered trademark, manufactured by Promega). This tag is immobilized by covalent binding onto HaloLink Magnetic Beads (trade name, manufactured by Promega) (TAL-conjugated beads, see FIG. 2B). Another example of the tag is a GST tag. This tag is immobilized by affinity binding onto Glutathione Sepharose 4B (manufactured by GE Healthcare).

(3) If needed, cells to be analyzed are stimulated. If needed, in order to maintain the interaction of the genomic DNA with proteins, RNAs, DNAs and other interacting molecules in the genomic region to be isolated, the cells are subjected to crosslinking treatment with a crosslinking agent such as formaldehyde (see the top of FIG. 2C).

(4) The cells are lysed, and the genomic DNA in a state where the interaction is maintained is digested with a deoxyribonuclease(s) such as a restriction enzyme for fragmentation. Alternatively, the fragmentation may be performed by ultrasonication. This step produces a DNA fragment containing the endogenous DNA sequence to which the TAL-conjugated beads bind, and a DNA fragment(s) not containing the endogenous DNA sequence.

(5) The DNA fragment containing the endogenous DNA sequence to which the TAL-conjugated beads bind binds to the TAL-conjugated beads (see the bottom of FIG. 2C).

(6) The TAL-conjugated beads are harvested and thereby the desired genomic region can be isolated. The isolated genomic region remains bound to molecules interacting therewith. Therefore, after the interaction (crosslinks) is eliminated, the interacting molecules such as proteins, RNAs, DNAs and other molecules can be purified and identified.

<Use of Isolated Specific Genomic Regions>

The specific genomic region isolated by the method of the present invention is very useful as a sample for the analysis of the molecular mechanisms of genome functions. Since the isolated specific genomic region is in a state where the interaction of genomic DNA and molecules interacting therewith (proteins, DNAs, RNAs, etc.) is maintained, identification of the interacting molecules and deduction of their functions are feasible. Therefore, the method of the present invention is expected to greatly contribute to the analysis of the molecular mechanisms of genome functions.

The identification of the interacting molecules in the isolated specific genomic region can be performed by an appropriate combination of known methods without particular limitation. This can be achieved, for example, by eliminating the interaction, separating and purifying the interacting molecules, and employing a known identification method(s). In the case where the treatment for maintaining the interaction is crosslinking with formaldehyde, the crosslinks can be reversed by addition of a high concentration salt solution (5 M NaCl solution etc.) and subsequent incubation at a suitable temperature for a suitable duration (for example, at about 65° C. overnight). Examples of the known identification method for proteins include mass spectrometry, immunoblot and ELISA (enzyme-linked immunosorbent assay). Examples of the known identification method for DNAs or RNAs include nucleotide sequence analysis, microarray analysis and PCR (polymerase chain reaction).

EXAMPLES

Hereinafter, the present invention will be illustrated in detail by examples, but the present invention is not limited thereto.

Example 1

Isolation of Telomeric Region (1) Preparation of Cells to be Analyzed

Cells expressing a TAL effector protein which recognizes telomeric TTAGGG repeats were prepared as follows. A DNA encoding Telomere-TAL, which is capable of binding to a 19-mer double-stranded DNA containing the telomeric TTAGGG repeats (TAGGGTTAGGGTTAGGGTT: SEQ ID NO: 1) was synthesized. The DNA synthesis was outsourced to Life Technologies. A retrovirus vector for expression of a fusion protein 3×FN-Tel-TAL (SEQ ID NO: 2), in which Telomere-TAL is fused with a 3×FLAG tag and a nuclear localization signal (NLS), was prepared (hereinafter, this expression vector is called 3×FN-Tel-TAL/pMXs-puro), a murine hematopoietic cell line Ba/F3 was infected with 3×FN-Tel-TAL/pMXs-puro, and only successfully infected cells were selected in the presence of puromycin. The amino acid sequence of the 3×FN-Tel-TAL protein is represented by SEQ ID NO: 2.

Negative control cells were prepared as follows. A retrovirus vector for expression of a fusion protein 3×FNLDD, which consists of a 3×FLAG tag, an NLS and a bacterial LexA protein (Fujita and Fujii, Adv. Biosci. Biotechnol. 3, 626-629 (2012)), was prepared (hereinafter, this expression vector is called 3×FNLDD/pMXs-puro), Ba/F3 cells were infected with 3×FNLDD/pMXs-puro, and only successfully infected cells were selected in the presence of puromycin.

Figure 3:
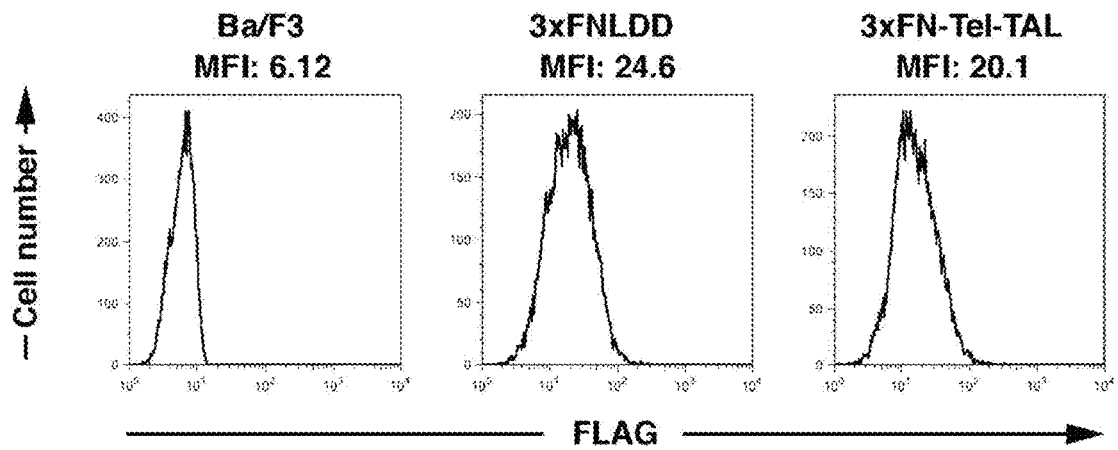
FIG. 3 shows the flow cytometric analysis of the expression levels of the indicated proteins in cells expressing 3×FN-Tel-TAL, which is a fusion protein of a TAL effector protein capable of binding to a telomeric sequence (Telomere-TAL), a 3×FLAG tag and a nuclear localization signal and in cells expressing a control protein (3×FNLDD).

To visualize the expression of the 3×FN-Tel-TAL protein and the 3×FNLDD protein, intracellular staining was performed using an anti-FLAG tag antibody (manufactured by Sigma-Aldrich, fluorescein isothiocyanate-conjugated anti-FLAG M2, F4049), followed by flow cytometry analysis. The results are shown in FIG. 3. In the figure, Ba/F3 (left) shows the results of intact host cells, 3×FNLDD (center) shows the results of the 3×FNLDD protein expressing cells, and 3×FN-Tel-TAL (right) shows the results of the 3×FN- Tel-TAL protein expressing cells. As is shown in FIG. 3, the expression levels of the 3×FN-Tel-TAL protein and the 3×FNLDD protein were comparable.

(2) Isolation of Specific Genomic Region (a) To a cell suspension containing $2 \times 10^7$ cells in 30 mL of RPMI complete medium supplemented with interleukin 3, 810 µL of 37% formaldehyde was added, and the cells were incubated at 37° C. for 5 minutes for crosslinking treatment. Next, 3 mL of a 1.25 M glycine solution was added, and a neutralization reaction was allowed to proceed at room temperature for 10 minutes.

(b) After centrifugation (at 1.3 krpm at 4° C. for 5 minutes), the cells were washed twice with ice-cold PBS, suspended in 10 mL of cell lysis buffer (10 mM Tris (pH 8.0), 1 mM EDTA, 0.5% IGEPAL CA-630, protease inhibitor cocktail), and the cell suspension was placed on ice for 10 minutes. After centrifugation (at 2.0 krpm at 4° C. for 8 minutes), the supernatant was discarded, the cell pellet was suspended in 10 mL of nuclear lysis buffer (10 mM Tris (pH 8.0), 1 mM EDTA, 0.5 M NaCl, 1% Triton X-100, 0.5% sodium deoxycholate, 0.5% lauroylsarcosine salt, protease inhibitor cocktail), and the cell suspension was placed on ice for 10 minutes with intermittent (2 to 3-minute interval) stirring using a vortex mixer. After centrifugation (at 2.0 krpm at 4° C. for 8 minutes), the supernatant was discarded, the cell pellet was washed with ice-cold PBS, and a chromatin fraction was obtained.

(c) The chromatin fraction was suspended in 800 µL of lysis buffer 3 (10 mM Tris (pH 8.0), 1 mM EDTA, 0.5 mM EGTA, 150 mM NaCl, 0.1% sodium deoxycholate, 0.1% SDS, protease inhibitor cocktail) and subjected to ultrasonication for fragmentation of the crosslinked genomic DNA (ultrasonic generator: manufactured by TOMY SEIKO, Ultrasonic disruptor UD-201, output: 3, duty: 100%, a set of 10 sec×6 with 20-sec intervals was repeated 3 times at 2-minute intervals (18 times in total)).

(d) After centrifugation (at 1.3 krpm at 4° C. for 10 minutes), the supernatant (800 µL) was harvested. To 160 µL (equivalent to $4 \times 10^6$ cells) of the supernatant, 240 µL of lysis buffer 3, 50 µL of lysis buffer 3 supplemented with 10% Triton X-100 and 50 µL of a 10× protease inhibitor solution were added to a total volume of 500 µL. This was precleared with Dynabeads conjugated with control IgG, and thereby non-specifically bound components were removed. Subsequently, immunoprecipitation using Dynabeads conjugated with an anti-FLAG antibody M2 (manufactured by Sigma-Aldrich, anti-FLAG M2, 811804) was performed.

(e) After washing, the immunoprecipitated complex was suspended in 300 µL of TE. After crosslink reversal, treatment with RNase A and Proteinase K was performed, followed by phenol/chloroform treatment to give a purified DNA.

(f) The obtained DNA was used for Southern blot analysis. For detection of the telomeric DNA, Telo TAGGG Telomerase Length Assay kit (12209136001, manufactured by Roche) was used.

Figure 4:
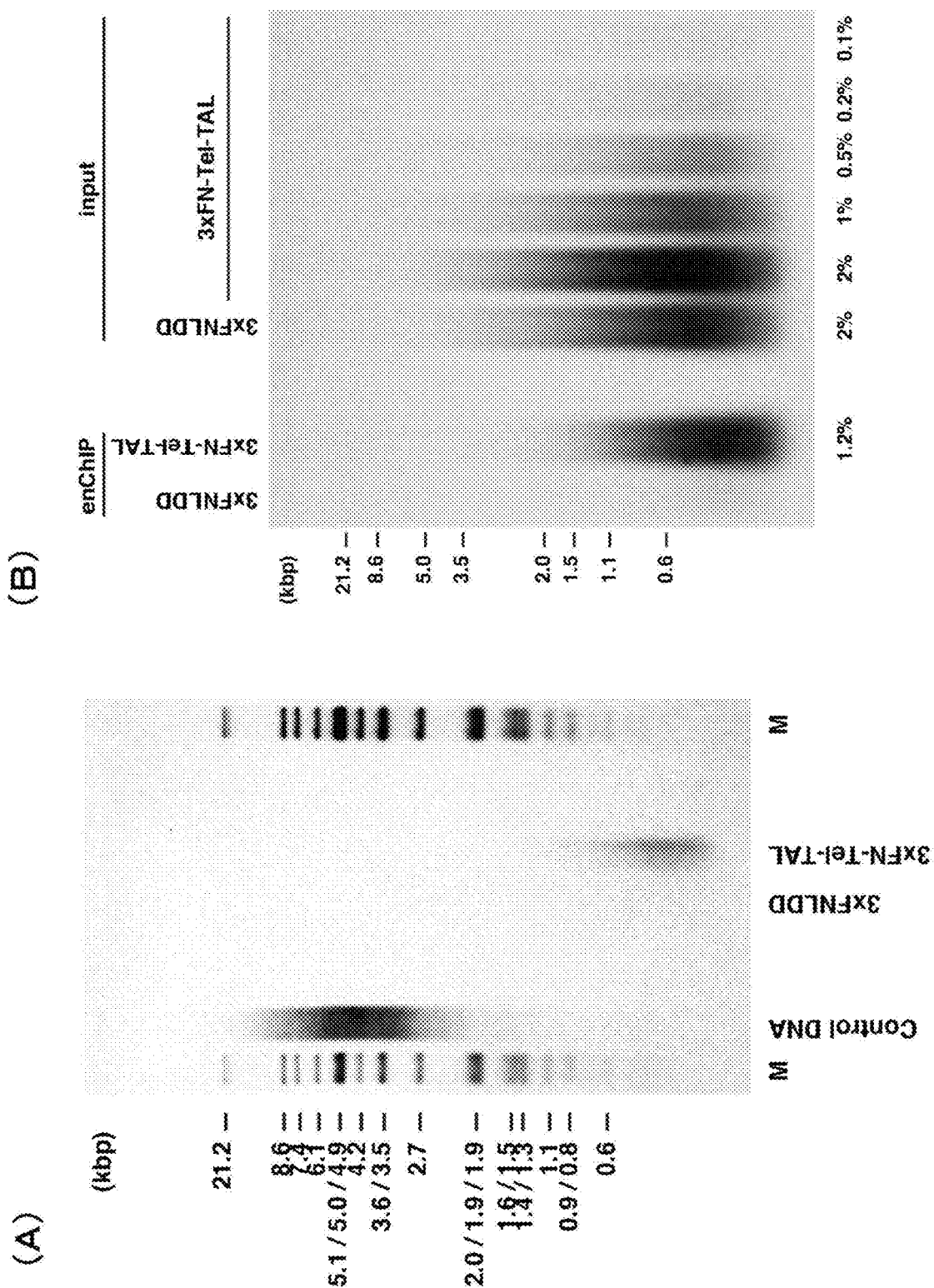
FIG. 4 shows successful isolation of the genomic DNA of the telomeric region using 3×FN-Tel-TAL in the Southern blot analysis using a probe against the telomeric sequence. (A) and (B) show the reproducibility of the results.

The results of the Southern blot analysis are shown in FIGS. 4 (A) and (B). (A) and (B) show the reproducibility of the results. As is clear from FIGS. 4 (A) and (B), in the Southern blot analysis of the two samples obtained by immunoprecipitation, the telomeric DNA was detected only in the immunoprecipitated complex containing 3×FN-Tel-TAL. These results show that the telomeric region can be harvested by immunoprecipitation using 3×FN-Tel-TAL.

(3) Identification of proteins contained in isolated telomeric region (g) The same procedures as in the above (a) to (d) were performed to give an immunoprecipitate. For the immunoprecipitation, 300 µL of Dynabeads and 30 µL of an antibody were used. To the obtained immunoprecipitate, 200 µL of a 3×FLAG peptide solution (manufactured by Sigma-Aldrich, F4799, 0.5 mg/mL) was added, and this was incubated at 37° C. for 20 minutes for elution from the beads. The eluate was precipitated with isopropanol, suspended in 40 µL of 2×SDS sample buffer, and incubated at 100° C. for 30 minutes to accomplish both protein degeneration and crosslink reversal.

(h) Subsequently, electrophoresis was performed on a 4-20% gradient SDS-PAGE gel until the sample migrated about 1.5 cm into the gel. After staining with Coomassie Brilliant Blue (CBB), the sample in the gel was divided into five fractions and subjected to mass spectrometry analysis.

The proteins detected more abundantly in the case of immunoprecipitation using 3×FN-Tel-TAL than using 3×FNLDD included many of the following proteins: known telomere-binding proteins, proteins known to interact with other telomere-binding proteins, and proteins genetically demonstrated to be involved in telomere functions (see Table 1). These results demonstrate that, according to the method of the present invention, proteins specifically binding to the sequence of a specific genomic region can be isolated as a chromatin complex and identified by mass spectrometry.

TABLE 1

| | |
|---|---|
| Mammalian telomere-binding proteins | PML, RPA, CDK1, PPAR1, PCBP1 |
| Telomere-binding proteins in yeast or other organisms | IMP4 |
| Proteins interacting with telomere-binding proteins (associated telomere-binding protein) | DNA polymerase α (Cdc13p), ARMC6 (TRF2), CTBP1 (FoxP2-POT1), exportin-5 (TERT), GNL3L (TRF1), exportin-1 (TERT), 14-3-3 (TERT) |
| Proteins localizing to heterochromatin | BEND3 |
| Proteins whose mutations affect telomere function | DNA polymerase α, HAT1, Nup133, CDK7, DPOE1, PRDX1, TYSY, glutamate-cysteine ligase, glutaredoxin, SMRC1 |

(4) Identification of RNA contained in isolated telomeric region (i) The same procedures as in the above (a) to (e) were performed to give an immunoprecipitate. All the buffers to be used were supplemented with RNasin Plus (Promega). After treatment with Proteinase K, RNA purification was performed using Isogen II (NIPPON GENE CO., LTD.).

(j) Subsequently, RT-PCR was performed using TITANIUM One-Step RT-PCR (Clontech) in an attempt to detect a telomerase RNA. The primers used for the RT-PCR were 5'-CCGGCGCCCCGCGGCTGACAGAG-3' (SEQ ID NO: 3) (for reverse transcription), 5'-GCTGTGGGTTCTGGTCTTTTGTTC-3' (SEQ ID NO: 4) and 5'-GCGGCAGCGGAGTCCTAAG-3' (SEQ ID NO: 5).

Figure 5:
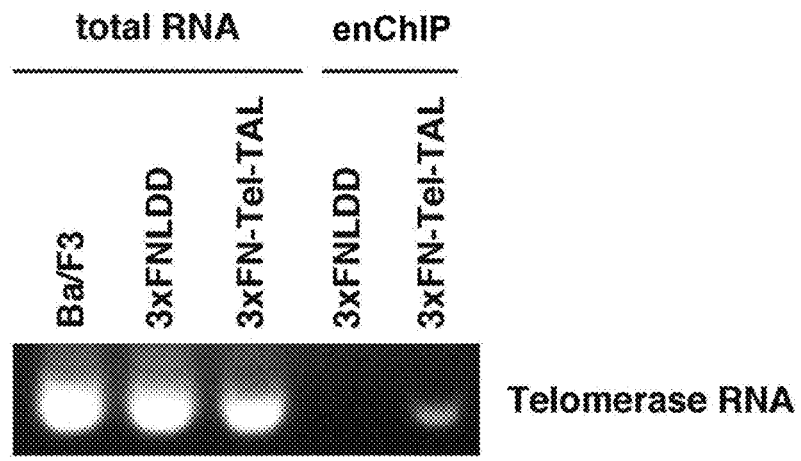
FIG. 5 shows the RT-PCR-based detection of a telomerase RNA contained in the isolated telomeric region.

The results of the RT-PCR are shown in FIG. 5. As is clear from FIG. 5, the telomerase RNA was detected only in the case of immunoprecipitation using 3×FN-Tel-TAL. These results demonstrate that, according to the method of the present invention, RNAs specifically binding to the sequence of a specific genomic region can be isolated as a chromatin complex and quantified by RT-PCR.

17

Example 2

Isolation of Sox2 Gene Promoter Region (1) Preparation of Cells to be Analyzed Cells expressing a TAL effector protein which recognizes a nucleotide sequence (TTATTCCCTGACA, SEQ ID NO: 6) present in the promoter region of the human Sox2 gene were prepared as follows. A DNA encoding the TAL effector protein recognizing the above sequence (SEQ ID NO: 6) was purchased from Addgene (Addgene #35388). A plasmid vector for expression of a fusion protein 3×FN-Sox2-TAL, in which the TAL effector protein is fused with a 3×FLAG tag and a nuclear localization signal (NLS), was prepared and transfected into human embryonic kidney 293T cells to prepare 3×FN-Sox2-TAL expressing cells.

Negative control cells were prepared as follows. A DNA encoding a TAL effector protein which recognizes a nucleotide sequence (TCTTACTTATAAC, SEQ ID NO: 7) present in the promoter region of the human KLF4 gene (Addgene #35389) and a DNA encoding a TAL effector protein which recognizes a nucleotide sequence (ACCACTCACTATA, SEQ ID NO: 8) present in the cytomegalovirus promoter region (Addgene #27970) were purchased from Addgene, and the same procedure as above was performed to prepare 3×FN-KLF4-TAL expressing cells and 3×FN-CMV-TAL8 expressing cells.

Figure 6:
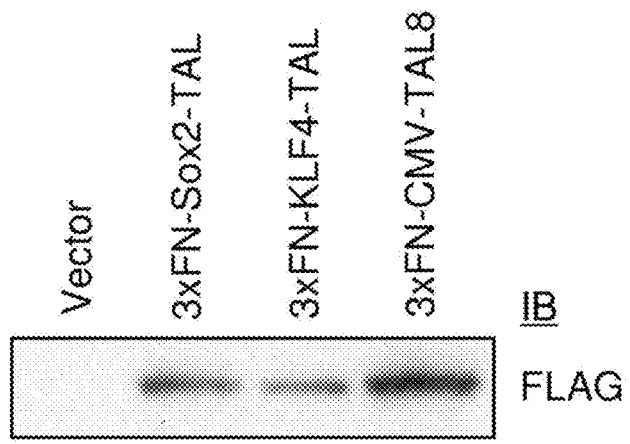
FIG. 6 shows the immunoblot analysis of the expression levels of the indicated proteins in cells expressing a TAL effector protein capable of binding to the DNA sequence of the promoter region of the human Sox2 gene (3×FN-Sox2-TAL) and in two types of cells expressing different types of control proteins.

The expression of these TAL effector proteins was confirmed by western blot using an anti-FLAG tag antibody (manufactured by Sigma-Aldrich, anti-FLAG M2, F1804). The results are shown in FIG. 6. As is shown in FIG. 6, the expression levels of these TAL effector proteins were comparable.

(2) Isolation of Specific Genomic Region (a) To a cell suspension containing $1.5 \times 10^7$ cells in 30 mL of DMEM complete medium, 810 III, of 37% formaldehyde was added, and the cells were incubated at 37° C. for 5 minutes for crosslinking treatment. Next, 3 mL of a 1.25 M glycine solution was added, and a neutralization reaction was allowed to proceed at room temperature for 10 minutes.

(b) to (d) The same procedures as in the above (b) to (d) of Example 1 (2) were performed for immunoprecipitation of the Sox2 promoter region to be analyzed.

(e) After washing, 40 µL of a 3×FLAG peptide solution (manufactured by Sigma-Aldrich, F4799, 0.5 mg/mL) was added to the obtained immunoprecipitate, and this was incubated at 37° C. for 30 minutes for elution from the beads. The eluted immunoprecipitate was suspended in 60 µL of TE and subjected to treatment with RNase A and Proteinase K, followed by crosslink reversal. After this, DNA purification was performed with ChIP DNA Clean & Concentrator-Capped column (manufactured by ZYMO RESEARCH, D5205).

Figure 7:
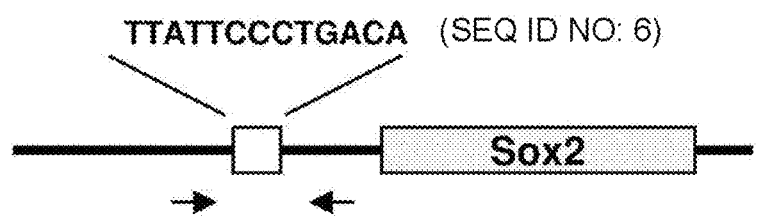
FIG. 7 shows a schematic view of the promoter region of the human Sox2 gene. The arrows represent primers used for real-time PCR.

(f) Real-time PCR was performed using the obtained DNA. The primers used for the real-time PCR were 5'-ATTGGTCGCTAGAAACCCATTTATT-3' (SEQ ID NO: 9) and 5'-CTGCCTTGACAACTCCTGATACTTT-3' (SEQ ID NO: 10). These primers were designed to flank the 3×FN-Sox2-TAL recognition sequence (TTATTCCCTGACA, SEQ ID NO: 6), which is present in the promoter region of the human Sox2 gene (see FIG. 7).

Figure 8:
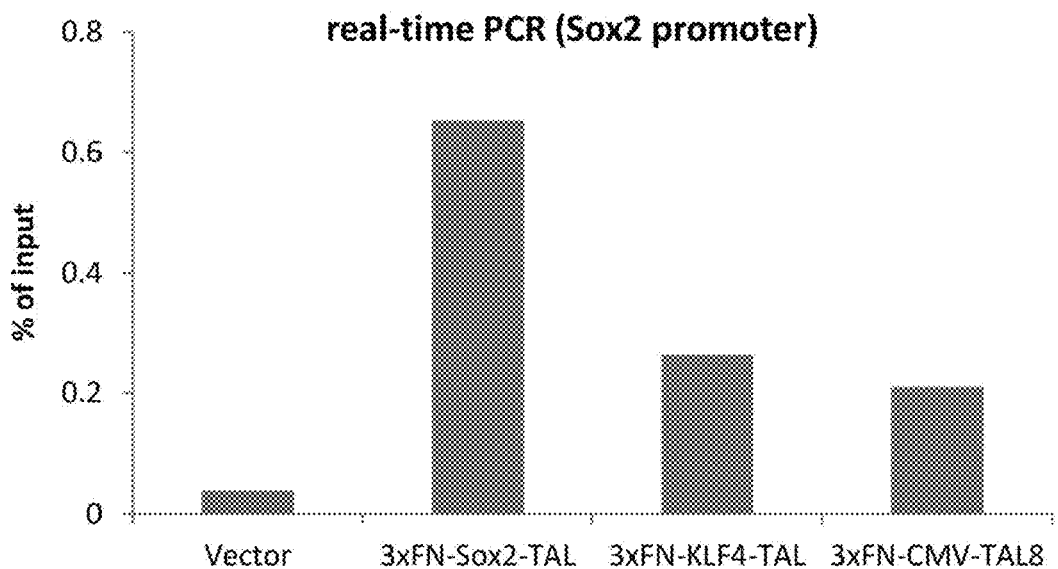
FIG. 8 shows the results of real-time PCR and demonstrates successful isolation of the genomic DNA of the promoter region of the human Sox2 gene using a TAL effector protein capable of binding to the DNA sequence of the promoter region of the human Sox2 gene (3×FN-Sox2-TAL).

The results of the real-time PCR are shown in FIG. 8. As is clear from FIG. 8, in the case of immunoprecipitation using 3×FN-Sox2-TAL, the Sox2 promoter region was enriched about 2.5 to 3 times as compared with the negative controls. These results show that the Sox2 promoter region can be harvested by immunoprecipitation using 3×FN-Sox2-

18

TAL. The above results indicate that the method of the present invention is applicable to even cases where the analyte of interest is a genomic region which is present at only one or two copies per cell.

Example 3

Isolation of IRF-1 Locus Using Inactive Cas9 Protein-RNA Complex (CRISPR System)

Figure 9:
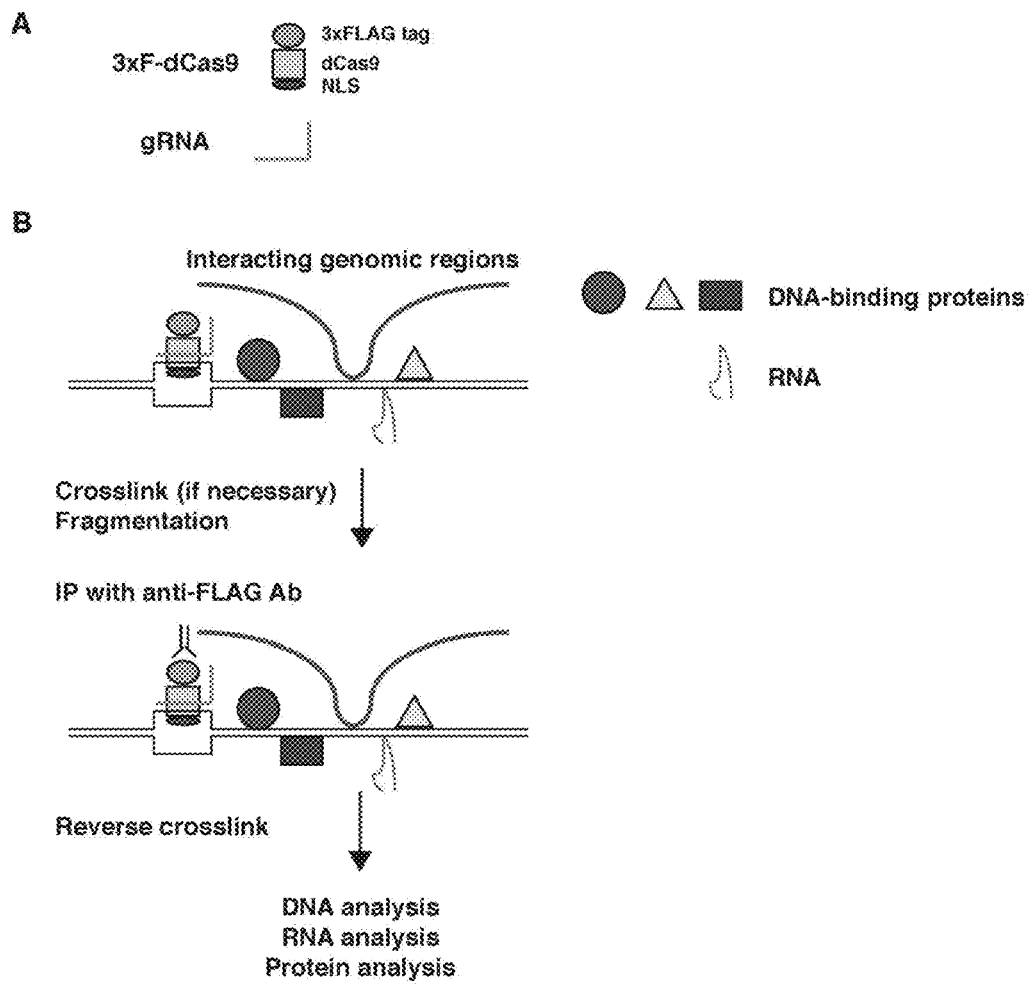
FIG. 9 shows the scheme of an embodiment of the method of the present invention for isolating a specific genomic region (a method for isolating a specific genomic region with the use of a complex of an inactive Cas9 protein and a gRNA (CRISPR system)).

The scheme of this Example is shown in FIG. 9.

(1) Preparation of CRISPR System to be Analyzed

A plasmid encoding a Cas9 D10A mutant bearing the nuclear localization signal of SV40 T antigen was purchased from Addgene (Addgene #41816). Into this plasmid, H840A mutation was introduced to prepare an enzymatically inactive Cas9 mutant (dCas9). The dCas9 coding sequence was inserted into p3×FLAG-CMV-7.1 (Sigma-Aldrich) to prepare a vector for expression of a dCas9 protein fused with a 3×FLAG tag (hereinafter, this expression vector is called 3×F-dCas9/pCMV-7.1). 3×F-dCas9/pCMV-7.1 was transfected to human embryonic kidney 293T cells for transient expression of 3×F-dCas9. In addition, 3×FNLDD/pCMV-7.1 was transfected to 293T cells for transient expression of 3×FNLDD, and the resulting cells were used for comparison with the 3×F-dCas9 expressing cells.

Figure 10:
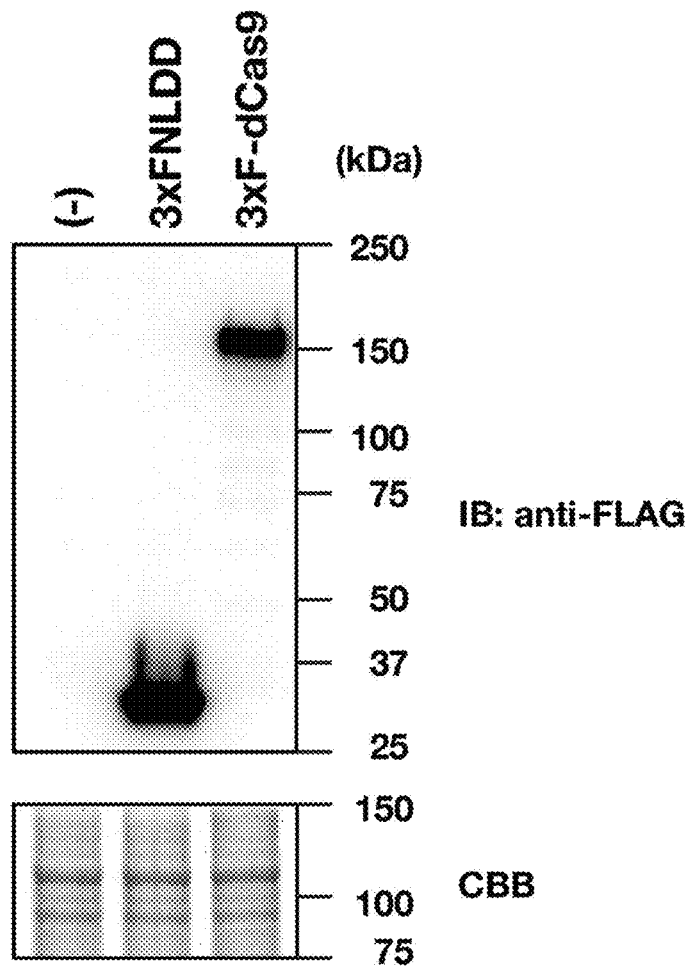
FIG. 10 shows the immunoblot analysis of the expression levels of the indicated proteins in cells expressing a dCas9 protein fused with a 3×FLAG tag (3×F-dCas9) and in cells expressing a control protein (3×FNLDD).

From each type of cells, a nuclear extract was prepared and subjected to western blot using an anti-FLAG tag antibody (manufactured by Sigma-Aldrich, anti-FLAG M2, F1804) for confirmation of the expression of 3×F-dCas9 and 3×FNLDD. The results are shown in FIG. 10. In the figure, (−) stands for intact host cells. The image of CBB staining shown in the lower panel indicates that the same amounts of samples were loaded in all the lanes. The results of the western blot show that the expression levels of 3×F-dCas9 and 3×FNLDD were comparable.

Next, according to Mali et al., Science (2013) 339: 823-826, an expression vector for a gRNA corresponding to the sequence 5'-CCGGGGGCGCTGGGCTGTCCCGG-3' (SEQ ID NO: 11), which is present in the human IRF-1 locus, was constructed as follows. The following two oligonucleotides: 5'-TTTCTTGGCTTTATATATCTTGTG-GAAAGGACGAAACACCGCGGGGGCGCTGGGCTG-TCC-3' (SEQ ID NO: 12) and 5'-GACTAGCCTTATTT-TAACTTGCTAT-TTCTAGCTCTAAAACGGACAGCCCAGCGCCCCGC-3' (SEQ ID NO: 13) were annealed, and using Phusion polymerase (New England BioLabs Inc.), a 100-bp double-stranded DNA fragment was synthesized. This fragment was purified by agarose electrophoresis and ligated to a gRNA cloning vector (Addgene #41824) using Gibson Assembly Kit (New England BioLabs Inc.) to prepare a vector for expression of the gRNA (hereinafter, this expression vector is called gRNA-hIRF-1 #12).

(2) Isolation of Human IRF-1 Locus (a) The above-prepared 3×F-dCas9/pCMV-7.1 and gRNA-hIRF-1 #12 were transfected into human embryonic kidney 293T cells ($3 \times 10^6$ cells) with the use of Lipofectamine 2000 (Invitrogen). On the day after the transfection, the cells were reseeded. On the following day, 810 µL of 37% formaldehyde was added to the cells in 30 mL of DMEM complete medium, and the cells were incubated at 37° C. for 5 minutes for crosslinking treatment. Next, 3 mL of a 1.25 M glycine solution was added, and a neutralization reaction was allowed to proceed at room temperature for 10 minutes.

(b) to (d) The same procedures as in the above (b) to (d) of Example 1 (2) were performed for immunoprecipitation of the IRF-1 region to be analyzed.

(e) After washing, the immunoprecipitated complex was suspended in 285 μL of TE. After addition of 12 μL of 5 M NaCl, incubation was continued at 65° C. overnight for crosslink reversal. Subsequently, treatment with RNase A and Proteinase K was performed, followed by phenol/chloroform treatment to give a purified DNA.

(f) Real-time PCR was performed using the obtained DNA. The primers used for the real-time PCR were 5'-CGCCTGCGTTCGGGAGATATAC-3' (SEQ ID NO: 14) and 5'-CTGTCCTCTCACTCCGCCTTGT-3' (SEQ ID NO: 15). These primers were designed to anneal to the vicinity of the target DNA sequence of the human IRF-1 locus. In addition, the primers of SEQ ID NO: 9 and 10 were used for the quantification of the Sox2 locus, which is an unrelated region.

Figure 11:
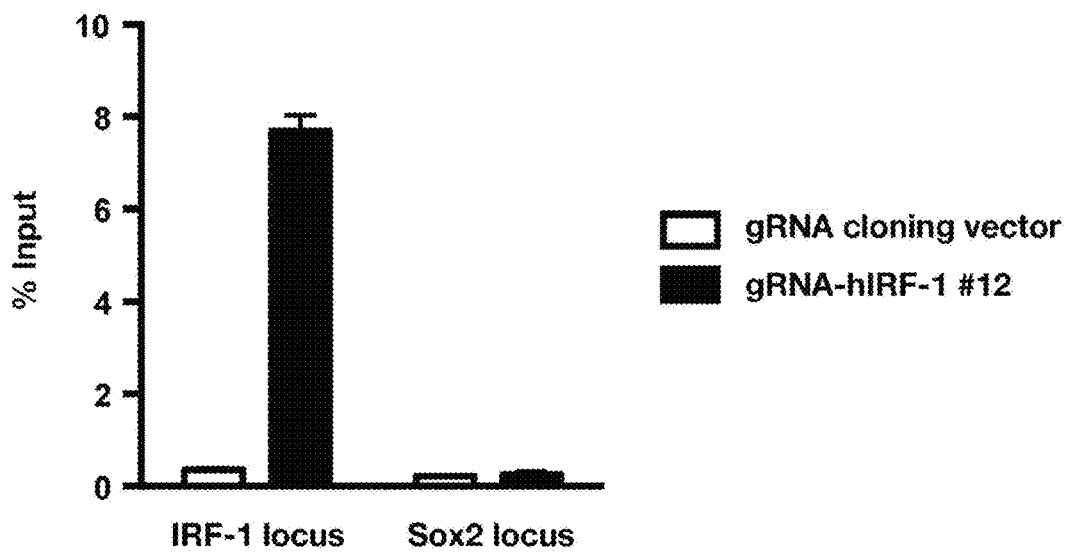
FIG. 11 shows the results of real-time PCR and demonstrates successful isolation of the genomic DNA of the human IRF-1 locus using a gRNA corresponding to a sequence present in the human IRF-1 locus (gRNA-hIRF-1 #12) and a dCas9 protein fused with a 3×FLAG tag (3×F-dCas9).

The results of the real-time PCR are shown in FIG. 11. As is clear from FIG. 11, the IRF-1 locus was hardly enriched in the negative control, and in contrast, in the case where 3×F-dCas9 and gRNA-hIRF-1 #12 were used, the percent of enrichment compared to the input was as high as 7.7%. The unrelated Sox2 locus was not enriched at all. These results show that the target locus can be harvested specifically and efficiently by immunoprecipitation using 3×F-dCas9 and the gRNA. The above results indicate that the method of the present invention is applicable to even cases where the analyte of interest is a genomic region which is present at only one or two copies per cell.

(3) Identification of Proteins Contained in Isolated IRF-1 Region (g) The same procedures as in the above (a) to (d) were performed to give an immunoprecipitate. For the immunoprecipitation, 300 μL of Dynabeads and 30 μL of an antibody were used. To the obtained immunoprecipitate, 200 μL, of a 3×FLAG peptide solution (manufactured by Sigma-Aldrich, F4799, 0.5 mg/mL) was added, and this was incubated at 37° C. for 20 minutes for elution from the beads. The eluate was precipitated with isopropanol, suspended in 40 μL of 2×SDS sample buffer, and incubated at 100° C. for 30 minutes to accomplish both protein degeneration and crosslink reversal.

Figure 12:
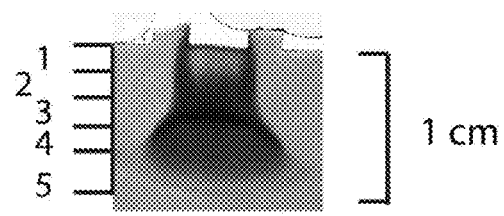
FIG. 12 shows that a sample intended for mass spectrometry-based identification of the proteins contained in the isolated IRF-1 region was electrophoresed on a SDS-PAGE gel until the sample migrated about 1.0 cm into the gel, and after staining with Coomassie Brilliant Blue, divided into five fractions.

(h) Subsequently, electrophoresis was performed on a 4-20% gradient SDS-PAGE gel until the sample migrated about 1.0 cm into the gel. After staining with CBB, the sample in the gel was divided into five fractions and subjected to mass spectrometry analysis (see FIG. 12).

The detected proteins included many of the following proteins: known protein components of chromatin such as histones, histone binding proteins, metabolic enzyme proteins and RNA helicases (see Table 2). These results demonstrate that, according to the method of the present invention, proteins binding to the sequence of a specific genomic region can be isolated as a chromatin complex and identified by mass spectrometry.

TABLE 2

| Protein |
| --- |
| Histones: H1, H2A, H2B, H3, H4 |
| Histone-binding protein RBBP7 |
| Metabolic enzymes: pyruvate kinase isoenzymes M1/M2, alpha-enolase, fatty acid synthase, creatinine kinase B, fructose-bisphosphate aldolase A, poly[ADP-ribose] polymerase, peroxiredoxin-1/2, phosphoglycerate kinase 1, L-lactate dehydrogenase B |
| RNA helicases: DDX1, DDX3X, DDX6, DDX17, DDX21, DDX39B |
| Elongation factors: 1-α, 1-γ, 1-δ, 2 |
| Tubulins: α-1B, β-5, β-4B |
| Eukaryotic translation initiation factors |
| Peptidyl-prolyl cis-trans isomerases: A, FKBP4 |
| Actin and actin-related proteins: actin-5C, actin-related protein 2/3 complex subunit 4, actin-related protein 3B |
| Nucleolin |
| Ribosomal proteins |
| Polyadenylate-binding protein 1 |
| T-complex proteins |
| Heat Shock proteins: HSP7C, HSP70-1A/1B, HSP70-4, HSP90-α, HSP90-β, HS105 |

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for isolating a specific genomic region while maintaining an interaction of the specific genomic region and molecules interacting therewith, the method comprising the following steps 1 to 3:
   step 1: bringing genomic DNA in cells into contact with an exogenous molecule which binds to a specific endogenous DNA sequence in the genomic DNA, wherein the cells do not have a recognition sequence of the exogenous molecule inserted therein,
   step 2: fragmenting the genomic DNA in the cells in a state where the interaction of the specific genomic region and molecules interacting therewith is maintained, and
   step 3: allowing a genomic DNA fragment bound to the exogenous molecule to form a complex with a molecule which specifically binds to the exogenous molecule, and then harvesting the complex,
   wherein the exogenous molecule is a complex of an inactive Cas9 protein and a guide RNA (gRNA), and wherein the molecules interacting therewith are selected from the group consisting of proteins, DNAs, and RNAs.

2. The method according to claim 1, further comprising a step, between steps 1 and 2, of performing a treatment for maintaining the interaction of specific genomic region and molecules interacting therewith.

3. The method according to claim 1, wherein the exogenous molecule is a fusion molecule containing one or more kinds of tag sequences.

4. The method according to claim 1, wherein the exogenous molecule is a fusion molecule having a nuclear localization signal(s).

5. A method for analyzing the molecular mechanisms of genome functions, the method comprising the following steps of:
   isolating a specific genomic region by the method according to claim 1, and
   identifying molecules interacting with the genomic DNA of the isolated specific genomic region by one or more selected from the group consisting of mass spectrometry, immunoblot, ELISA, nucleotide sequence analysis, microarray analysis and PCR.

* * * * *